United States Patent [19]

Lamm et al.

[11] Patent Number: 5,380,859
[45] Date of Patent: Jan. 10, 1995

[54] PYRIDONE COMPOUNDS AND THE PREPARATION OF DISULFONATED PYRIDONE COMPOUNDS

[75] Inventors: Gunther Lamm, Hassloch; Helmut Beichelt, Neustadt; Ortwin Schaffer, Ludwigshafen, all of Germany

[73] Assignee: Basf Aktiengesellschaft, Ludwigshafen, Germany

[21] Appl. No.: 87,792

[22] PCT Filed: Feb. 10, 1992

[86] PCT No.: PCT/EP92/00281

§ 371 Date: Jul. 16, 1993

§ 102(e) Date: Jul. 16, 1993

[87] PCT Pub. No.: WO92/14791

PCT Pub. Date: Sep. 3, 1992

[30] Foreign Application Priority Data

Feb. 20, 1991 [DE] Germany ............... 4105257

[51] Int. Cl.$^6$ .......... C07D 211/72; C07D 211/84; C07D 213/62; C07D 213/69; C09D 29/42; C09D 31/153

[52] U.S. Cl. .......... 546/296; 534/772; 534/861; 534/869; 534/642; 534/730; 534/757; 534/764; 534/583; 534/784; 534/785; 534/782; 534/773; 534/821; 534/827; 534/836; 534/837; 534/845; 534/851; 546/294

[58] Field of Search .......... 534/772, 861, 869; 546/294, 296

[56] References Cited

U.S. PATENT DOCUMENTS

| | | | |
|---|---|---|---|
| 3,763,170 | 10/1973 | Austin et al. | 546/296 X |
| 3,867,392 | 2/1975 | Heinrich et al. | 546/296 X |
| 3,912,744 | 10/1975 | Heinrich et al. | 546/294 |
| 5,153,356 | 10/1992 | Lamm et al. | 562/46 |

FOREIGN PATENT DOCUMENTS

| | | | |
|---|---|---|---|
| 0121495 | 10/1984 | European Pat. Off. | 534/772 |
| 0126324 | 11/1984 | European Pat. Off. | 534/783 |
| 0154816 | 9/1985 | European Pat. Off. | 534/772 |
| 0302401 | 2/1989 | European Pat. Off. | 534/759 |
| 0413229 | 2/1991 | European Pat. Off. | 534/759 |
| 2138017 | 12/1972 | France | 534/772 |
| 2214727 | 8/1974 | France | 534/772 |
| 2004487 | 8/1971 | Germany | 534/772 |
| 2117753 | 10/1972 | Germany | 546/394 |
| 61-043673 | 3/1986 | Japan | 534/862 |

*Primary Examiner*—Floyd D. Higel
*Attorney, Agent, or Firm*—Oblon, Spivak, McClelland, Maier & Neustadt

[57] ABSTRACT

There are described benzophenoneazo dyes of the formula

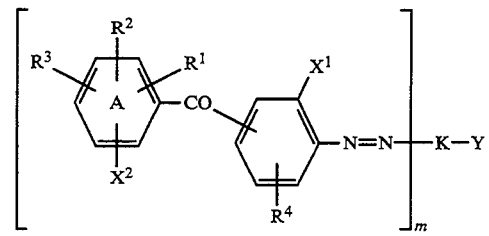

where
the ring A can be benzofused and a benzofused ring A can be overbridged,
m is 1 or 2,
K is the radical of a coupling component,
Y is hydrogen or arylazo,
one of the two radicals $X^1$ and $X^2$ is hydrogen and the other is hydroxysulfonyl,
$R^1$, $R^2$ and $R^3$ are independently of the others hydrogen, halogen, $C_1$-$C_{12}$-alkyl, cyclohexyl, phenyl, 2-hydroxyethylsulfonyl or $C_1$-$C_4$-alkoxy or, when m is 1 and Y is hydrogen, one of these substituents can also be the radical of the formula (Abstract continued on next page.)

ABSTRACT

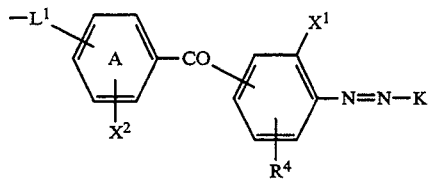

where $L^1$ is a chemical bond or a bridge member, and $X^1$, $X^2$, $R^4$, K and the ring A are each as defined above, and $R^4$ is hydrogen, halogen or $C_1$-$C_4$-alkoxy, with the proviso that there is at least one water-solubilizing group in the molecule, novel pyridone compounds, a process for preparing disulfonated pyridone compounds, and the use of the novel dyes for dyeing natural or synthetic substrates.

2 Claims, No Drawings

PYRIDONE COMPOUNDS AND THE PREPARATION OF DISULFONATED PYRIDONE COMPOUNDS

The present invention relates to a novel benzophenoneazo dye of the formula I

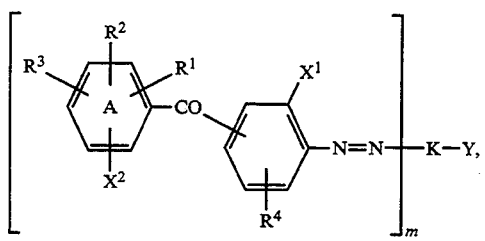

where
the ring A can be benzofused and a benzofused ring A can be bridged by $C_2H_4$,
m is 1 or 2,
K is the radical of a 6-hydroxypyrid-2-one derivative which in ring position 3 is unsubstituted or substituted by carbamoyl, $C_2$–$C_5$-alkanoyl, hydroxysulfonylmethyl or hydroxysulfonyl, or is the radical of a coupling component of the phenylazopyridone, diaminopyridine, imidazolopyridine, aminopyrazole, hydroxypyrazole, aminothiazole, pyrimidine, indole, quinolone, aniline or aminonaphthalene series,
Y, when m is 1, is hydrogen or the radical —N═N—Q, where Q is the radical of a diazo or coupling component, or, when m is 2, is hydrogen,
$X^1$ and $X^2$ are identical or different and each is independently of the other hydrogen or hydroxysulfonyl,
$R^1$, $R^2$ and $R^3$ are identical or different and each is independently of the others hydrogen, halogen, $C_1$–$C_{12}$-alkyl, cyclohexyl, phenyl, 2-hydroxyethylsulfonyl or $C_1$–$C_4$-alkoxy or, when m is 1 and Y is hydrogen, one of these substituents can also be the radical of the formula one of the two radicals $X^1$ and $X^2$ is hydrogen and the other hydroxysulfonyl,
$R^1$, $R^2$ and $R^3$ are identical or different and each is independently of the others hydrogen, halogen, $C_1$–$C_{12}$-alkyl, cyclohexyl, phenyl, 2-hydroxyethylsulfonyl or $C_1$–$C_4$-alkoxy or, when m is 1 and Y is hydrogen, one of these substituents can also be the radical of the formula

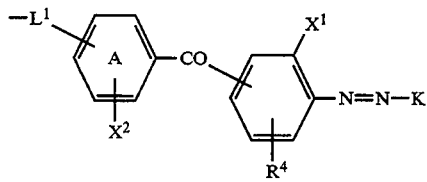

where
$L^1$ is a chemical bond, $C_1$–$C_4$-alkylene, oxygen or a radical of the formula O—$CH_2$, O—$CH_2CH_2$—O, O—$CH_2CH_2CH_2$—O or O—$CH(CH_3)CH_2$—O, and $X^1$, $X^2$, $R^4$, K and the ring A are each as defined above, and
$R^4$ is hydrogen, halogen or $C_1$–$C_4$-alkoxy, to novel pyridone compounds, to a process for preparing disulfonated pyridone compounds, and to the use of the novel dyes for dyeing natural or synthetic substrates.

The novel benzophenoneazo dyes of the formula I are shown in the form of the free acid. However, their salts are of course also included.

The salts in question are metal or ammonium salts. Metal salts are in particular the lithium, sodium or potassium salts. Ammonium salts suitable for the purposes of the present invention are those salts which have either substituted or unsubstituted ammonium cations. Substituted ammonium cations are for example monoalkyl-, dialkyl-, trialkyl-, tetraalkyl- or benzyltrialkyl-ammonium cations or those cations which are derived from nitrogen-containing five- or six-membered saturated heterocycles, such as pyrrolidinium, piperidinium, morpholinium, piperazinium or N-alkylpiperazinium cations or their N-monoalkyl- or N,N-dialkyl-substituted products. Alkyl here is to be understood as meaning in general straight-chain or branched $C_1$–$C_{20}$-alkyl, which can be substituted by hydroxyl groups and/or interrupted by oxygen atoms.

EP-A-302,401 and the earlier patent application EP-A 413 229 disclose benzophenoneazo dyes which, however, have no water-solubilizing group in the molecule.

DE-A-2 223 622 describes a dye with 3-aminobenzophenone-4-sulfonic acid as diazo component and 1-methyl-6-hydroxy-3,4-trimethylenepyrid-2-one as coupling component.

Furthermore, DE-A-3 316 887 describes an azo dye whose coupling component is 1-hydroxysulfonylbenzyl-3-hydroxysulfonyl-4-methyl-6-hydroxypyrid-2-one.

EP-A-154 816 discloses azo dyes with 4-aminobenzophenone as diazo component and diaminopyridines as coupling component.

Finally, EP-A-126 324 describes a phenylazo dye with a sulfonated N-benzylpyridone as coupling component.

It is an object of the present invention to provide novel benzophenoneazo dyes which have at least one hydroxysulfonyl group in the molecule and advantageous application properties.

We have found that this object is achieved by the benzophenoneazo dyes of the formula I defined at the beginning.

Any alkyl or alkylene appearing in the above-mentioned formula I may be either straight-chain or branched.

If substituted phenyl groups appear in the formulae of the dyes of the invention, they generally have from 1 to 3 substituents. Suitable substituents are for example $C_1$–$C_4$-alkyl, $C_1$–$C_4$-alkoxy, halogen and hydroxysulfonyl.

Coupling components KH of the pyridone or phenylazopyridone series conform for example to the formula IIc

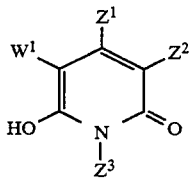

where
$W^1$ is hydrogen or a radical of the formula

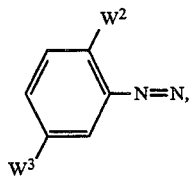

where
- $W^2$ and $W^3$ are identical or different and each is independently of the other hydrogen, methyl, ethyl or methoxy,
- $Z^1$ is hydrogen, $C_1$–$C_4$-alkyl or phenyl,
- $Z^2$ is hydrogen, carbamoyl, $C_2$–$C_5$-alkanoyl, hydroxysulfonylmethyl or hydroxysulfonyl, and
- $Z^3$ is hydrogen or $C_1$–$C_8$-alkyl which may be substituted by phenyl or hydroxysulfonylphenyl and may be interrupted by from 1 to 3 oxygen atoms in ether function.

Coupling components KH of the imidazolopyridine series conform for example to the formula IIe Coupling components KH of the quinolone series conform for example to the formula IIh

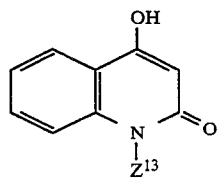

where
$Z^{13}$ is $C_1$–$C_4$-alkyl.

Coupling components KH of the pyrimidine series conform for example to the formula IIi or IIj

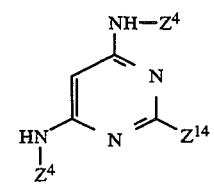

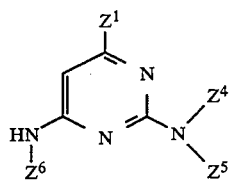

where
$Z^{14}$ is $C_1$–$C_4$-alkyl or phenyl, and
$Z^1$, $Z^4$, $Z^5$ and $Z^6$ are each as defined above.

Coupling components KH of the aniline series conform for example to the formula Ill

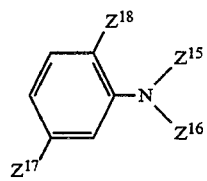

where
- Z15 is hydrogen or $C_1$–$C_6$-alkyl which may be unsubstituted or substituted by hydroxyl, $C_1$–$C_4$-alkoxy, cyano, $C_1$–$C_4$-alkanoyloxy, $C_1$–$C_4$-alkoxycarbonyloxy, $C_1$–$C_4$-alkylaminocarbonyloxy, phenyl, hydroxysulfonylphenyl, $C_1$–$C_4$-alkoxycarbonyl or chlorine-, hydroxyl-, $C_1$–$C_4$-alkoxy- or phenoxy-substituted $C_1$–$C_4$-alkoxycarbonyl,
- $Z^{16}$ is hydrogen or $C_1$–$C_6$-alkyl which may be substituted by phenyl, hydroxysulfonylphenyl, $C_1$–$C_4$-alkoxycarbonyl or chlorine-, hydroxyl-, $C_1$–$C_4$-alkoxy- or phenoxy-substituted $C_1$–$C_4$-alkoxycarbonyl,
- $Z^{17}$ is hydrogen, $C_1$–$C_4$-alkyl, $C_1$–$C_4$-alkoxy, chlorine, bromine or the radical —NH—CO—Q, where Q is $C_1$–$C_4$-alkyl, which may be $C_1$–$C_4$-alkoxy-, phenoxy-, cyano-, hydroxyl-, chlorine- or $C_1$–$C_4$-alkanoyloxy-substituted, or unsubstituted or $C_1$–$C_4$-alkoxy-substituted phenoxy, and
- $Z^{18}$ is hydrogen, $C_1$–$C_4$-alkyl or $C_1$–$C_4$-alkoxy.

If Y is the radical —N=N—Q, Q is the radical of a diazo or coupling component.

Suitable diazo components $Q^1$—$NH_2$ are derived for example from the aniline series. They conform for example to the formula III

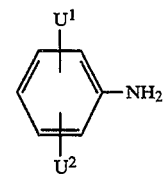

where
- $U^1$ is hydrogen, $C_1$–$C_4$-alkyl or hydroxysulfonyl and
- $U^2$ is hydrogen, unsubstituted or sulfato-substituted $C_1$–$C_4$-alkyl, hydroxysulfonyl, phenylsulfonyloxy or 6-methyl - 7-hydroxysulfonylbenzothiazol-2-yl.

Suitable coupling components $Q^2$—H are for example the abovementioned compounds of the formulae IIc, IIe, IIf, IIg, IIh, IIi, IIj, III or IIm, of which coupling components of the formula IIg are particularly noteworthy.

Radicals $R^1$, $R^2$, $R^3$, $Z^1$, $Z^2$, $Z^3$, $Z^4$, $Z^5$, $Z^6$, $Z^8$, $Z^9$, $Z^{10}$, $Z^{11}$, $Z^{12}$, $Z^{13}$, $Z^{14}$, $Z^{15}$, $Z^{16}$, $Z^{17}$, $Z^{18}$, $U^1$ and $U^2$ are each for example methyl, ethyl, propyl, isopropyl, butyl, isobutyl or sec-butyl.

Radicals $R^1$, $R^2$, $R^3$, $Z^3$, $Z^4$, $Z^5$, $Z^6$, $Z^{11}$, $Z^{12}$, $Z^{15}$ and $Z^{16}$ may each also be for example pentyl, isopentyl, neopentyl, tert-pentyl or hexyl.

Radicals $R^1$, $R^2$, $R^3$, $Z^3$, $Z^4$, $Z^5$, $Z^6$, $Z^{11}$ and $Z^{12}$ may each also be for example heptyl, octyl, 2-ethylhexyl or isooctyl.

Radicals $R^1$, $R^2$, $R^3$, $Z^4$, $Z^5$ and $Z^6$ may each also be for example nonyl, isononyl, decyl, isodecyl, undecyl or dodecyl. (The above designations isooctyl, isononyl and isodecyl are trivial names derived from oxo process alcohols—cf. Ullmanns Enzyklopädie der technischen Chemie, 4th edition, volume 7, pages 215 to 217, and also volume 11, pages 435 and 436.) are particularly noteworthy.

Radicals $R^1$, $R^2$, $R^3$, $Z^1$, $Z^2$, $Z^3$, $Z^4$, $Z^5$, $Z^6$, $Z^8$, $Z^9$, $Z^{10}$, $Z^{11}$, $Z^{12}$, $Z^{13}$, $Z^{14}$, $Z^{15}$, $Z^{16}$, $Z^{17}$, $Z^{18}$, $U^1$ and $U^2$ are each for example methyl, ethyl, propyl, isopropyl, butyl, isobutyl or sec-butyl.

Radicals $R^1$, $R^2$, $R^3$, $Z^3$, $Z^4$, $Z^5$, $Z^6$, $Z^{11}$, $Z^{12}$, $Z^{15}$ and $Z^{16}$ may each also be for example pentyl, isopentyl, neopentyl, tert-pentyl or hexyl.

Radicals $R^1$, $R^2$, $R^3$, $Z^3$, $Z^4$, $Z^5$, $Z^6$, $Z^{11}$ and $Z^{12}$ may each also be for example heptyl, octyl, 2-ethylhexyl or isooctyl.

Radicals $R^1$, $R^2$, $R^3$, $Z^4$, $Z^5$ and $Z^6$ may each also be for example nonyl, isononyl, decyl, isodecyl, undecyl or dodecyl. (The above designations isooctyl, isononyl and isodecyl are trivial names derived from oxo process alcohols—cf. Ullmanns Enzyklopädie der technischen Chemie, 4th edition, volume 7, pages 215 to 217, and also volume 11, pages 435 and 436.)

Radicals $Z^3$, $Z^4$, $Z^5$, $Z^6$, $Z^8$, $Z^{15}$ and $Z^{16}$ may each also be for example benzyl, hydroxysulfonylbenzyl, 1- or 2-phenylethyl or 1- or 2-(hydroxysulfonylphenyl)ethyl.

Radicals $Z^8$ and $Z^{10}$ may each also be for example phenyl, 2-, 3- or 4-methylphenyl, 2-, 3- or 4-methoxyphenyl, 2-, 3- or 4-chlorophenyl, 2,4-dichlorophenyl, 2-, 3- or 4-bromophenyl or 2-, 3- or 4-hydroxysulfonylphenyl.

Radicals $Z^3$, $Z^4$, $Z^5$, $Z^6$, $Z^{11}$ and $Z^{12}$ may each also be for example 2-methoxyethyl, 2-ethoxyethyl, 2-propoxyethyl, 2-isopropoxyethyl, 2-butoxyethyl, 2- or 3-methoxypropyl, 2- or 3-ethoxypropyl, 2- or 3-propoxypropyl, 2- or 3-butoxypropyl, 2- or 4-methoxybutyl, 2- or 4-ethoxybutyl, 2- or 4-propoxybutyl, 3,6-dioxa-heptyl, 3,6-dioxaoctyl, 4,8-dioxanonyl, 3,7-dioxaoctyl, 3,7-dioxanonyl, 4,7-dioxaoctyl, 4,7-dioxanonyl, 2- or 4-butoxybutyl, 4,8-dioxadecyl, 3,6,9-trioxadecyl or 3,6,9-trioxaundecyl.

Radicals $Z^4$, $Z^5$ and $Z^6$ may each also be for example 2-hydroxyethyl, 2- or 3-hydroxypropyl, 2- or 4-hydroxybutyl, 5-hydroxy-3-oxapentyl, 6-hydroxy-4-oxahexyl, 8-hydroxy-4-oxaoctyl, 9-hydroxy-4,7-dioxanonyl, 2-phenoxyethyl, 2- or 3-phenoxypropyl, 2- or 4-phenoxybutyl, 6-phenoxy-4-oxahexyl, 3,6,9,12-tetraoxatridecyl, 3,6,9,12-tetraoxatetradecyl, 2-formyloxyethyl, 2-acetyloxyethyl, 2- or 3-formyloxypropyl, 2- or 3-acetyloxypropyl, 2- or 4-formyloxybutyl, 2- or 4-acetyloxybutyl, 5-formyloxy-3-oxapentyl, 5-acetyloxy-3-oxapentyl, 6-formyloxy-4-oxaheptyl, 6-acetyloxy-4-oxyheptyl, 8-formyloxy-4-oxaoctyl, 8-acetyloxy-4-oxaoctyl, 9-formyloxy-4,7-dioxanonyl or 9-acetyloxy-4,7-dioxanonyl.

$Z^2$ is for example acetyl, propionyl, butyryl, isobutyryl or pentanoyl.

$Z^9$ may also be for example methoxycarbonyl, ethoxycarbonyl, propoxycarbonyl, isopropoxycarbonyl, butoxycarbonyl or isobutoxycarbonyl.

$R^{15}$ may also be for example 2-hydroxyethyl, 2- or 3-hydroxypropyl, 4-hydroxybutyl, 5-hydroxypentyl, 6-hydroxyhexyl, 2-methoxyethyl, 2-ethoxyethyl, 2-propoxyethyl, 2-butoxyethyl, 2-cyanoethyl, 2-formyloxyethyl, 2-acetyloxyethyl, 2-propionyloxyethyl, 2-butyryloxyethyl, 4-acetyloxybutyl, 2-methoxycarbonyloxyethyl, 2-methylaminocarbonyloxyethyl, 2-ethylaminocarbonyloxyethyl, 2-propylaminocarbonyloxyethyl or 2-butylaminocarbonyloxyethyl.

$Z^{15}$ and $Z^{16}$ may each also be for example 2-methoxycarbonylethyl, 2-ethoxycarbonylethyl, 2-propoxycarbonylethyl, 2-isopropoxycarbonylethyl, 2-butoxycarbonylethyl, 2-isobutoxycarbonylethyl, 2-sec-butoxycarbonylethyl, 2-(2-chloroethoxycarbonyl)ethyl, 2-(2-hydroxyethoxycarbonyl)ethyl, 2-(2-methoxyethoxycarbonyl)ethyl, 2-(2-ethoxyethoxycarbonyl)ethyl, 2-(2-propoxyethoxycarbonyl)ethyl, 2-(2-isopropoxycarbonyl)ethyl, 2-(2-butoxyethoxycarbonyl)ethyl or 2-(2-phenoxyethoxycarbonyl)ethyl.

When $Z^{17}$ is the radical NH—CO—Q, Q is for example methyl, ethyl, propyl, isopropyl, butyl, methoxymethyl, ethoxymethyl, 1- or 2-methoxyethyl, 1- or 2-ethoxyethyl, where m, K, Y, $X^1$, $X^2$, $R^1$, $R^2$, $R^3$ and $R^4$, are each as defined above.

Particular preference is given to benzophenoneazo dyes of the formula I where K is the radical of a 6-hydroxypyrid-2-one derivative which in ring position 3 is unsubstituted or substituted by carbamoyl, by $C_2$-$C_5$-alkanoyl, by hydroxysulfonylmethyl or by hydroxysulfonyl, the radical of a coupling component of the aminopyrazole or pyrimidine series, or a radical derived from the formula IIm.

Of note are benzophenoneazo dyes of the formula I where K is a radical of the formula IIc, IIf ($Z^7$=amino), IIi, IIj or IIm.

Also of note are benzophenoneazo dyes of the formula I where m is 1 and Y is hydrogen.

Also of note are benzophenoneazo dyes of the formula I where $R^1$, $R^2$ and $R^3$ are each independently of the other hydrogen, chlorine, $C_1$-$C_4$-alkyl, in particular methyl or ethyl, methoxy or ethoxy.

Of particular importance are benzophenoneazo dyes which conform to the formula Ib, Ic or Id

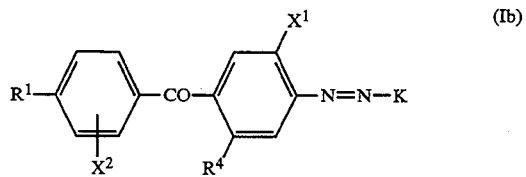 (Ib)

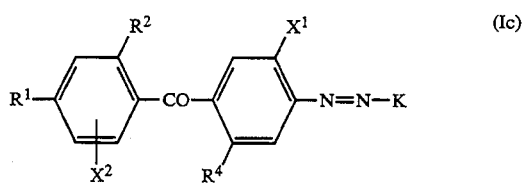 (Ic)

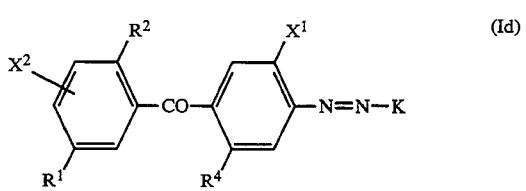 (Id)

where
one of the radicals $X^1$ and $X^2$ is hydrogen and the other is hydroxysulfonyl, $R^1$ and $R^2$ are independently of each other chlorine, $C_1$-$C_4$-alkyl, in particular methyl or ethyl, methoxy or ethoxy, $R^4$ is hydrogen or methoxy, and K is in each case as defined above.

Also of particular importance are benzophenoneazo dyes of the formula Ie or If

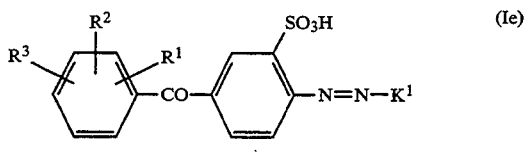 (Ie)

-continued

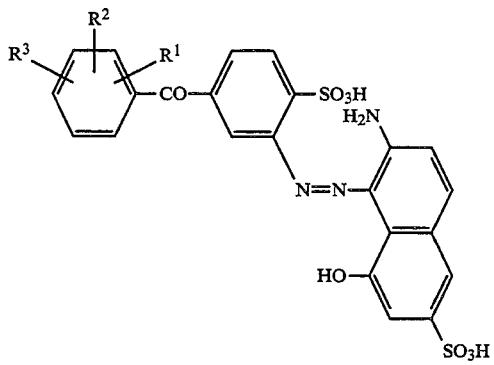
(If)

where
$R^1$, $R^2$ and $R^3$ are each as defined above and
$K^1$ is 1-phenyl-3-methyl-5-aminopyrazol-4-yl, 2-amino-6-hydroxysulfonyl-8-hydroxynaphth-1-yl or a radical of the formula IIo

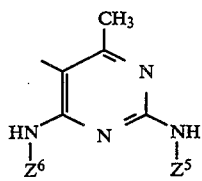
(IIo)

where
$Z^5$ and $Z^6$ are each as defined above.

Of industrial interest are benzophenoneazo dyes of the formula Ig

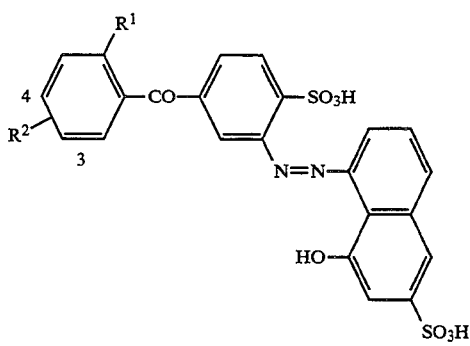
(Ig)

where
$R^1$ is hydrogen, $C_1$–$C_3$-alkyl or $C_1$–$C_4$-alkoxy, and
$R^2$ is $C_1$–$C_{12}$-alkyl, benzyl, phenylethyl or $C_1$–$C_4$-alkoxy in ring position 3 or 4, with the proviso that the total number of carbon atoms in the radicals $R^1$ and $R^2$ is from 4 to 12.

The novel aminobenzophenones of the formula I can be obtained in a conventional manner.

For example, an aminobenzophenone of the formula III

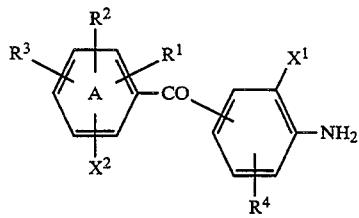
(III)

where $R^1$, $R^2$, $R^3$, $R^4$, $X^1$, $X^2$ and the ring A are each as defined above, is diazotized in a conventional manner and coupled with a coupling component of the formula IV

H—K—Y  (IV)

where K and Y are each as defined above.

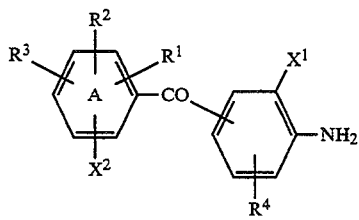
(III)

where $R^1$, $R^2$, $R^3$, $R^4$, $X^1$, $X^2$ and the ring A are each as defined above, is diazotized in a conventional manner and coupled with a coupling component of the formula IV

H—K—Y  (IV)

where K and Y are each as defined above. When m in the formula I is 2 and K—Y is the radical of a bivalent coupling component of the formula IId, generally twice the amount is used of the diazonium salt obtainable from the aminobenzophenone III.

When Y in the formula I is the radical $Q^1$—N=N—, the novel dyes can be obtained for example by first coupling the diazonium salt of the amine of the formula V $Q^1$—NH$_2$  (V)

where $Q^1$ is as defined above, with the coupling component of formula IVa

H—K—H  (IVa)

where K is as defined above, and coupling the resulting monoazo dye of the formula VI

H—K—N=N—$Q^1$  (VI)

where $Q^1$ and K are each as defined above, with the diazonium salt of the aminobenzophenone III. However, it is also possible to carry out the coupling reactions in the reverse order.

It is further possible to replace the amine of the formula V by an aminobenzophenone of the formula III, in which case the disazo dye obtained contains two different or identical radicals of the diazo component of the formula III.

If the coupling component of the formula IVa is of the aniline or naphthalene series (formula III or IIm)

and if it contains an unsubstituted amino group or a precursor thereof, the resulting monoazo dye of the formula VII

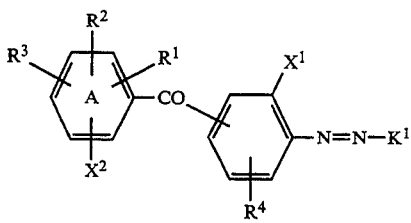 (VII)

where $K^1$ is the radical of a coupling component of the aniline or naphthalene series which has an amino group, and $R^1$, $R^2$, $R^3$, $R^4$, $X^1$, $X^2$ and the ring A are each as defined above, can also be diazotized again and coupled with a coupling component of the formula IVa. This again leads to disazo dyes.

The aminobenzophenones of the formula III are known compounds. They are described for example in the earlier European Patent Application No. 91112002.0.

The coupling components of the formula IV are likewise known products. They are described for example in D. R. Waring, G. Hallas, The Chemistry and Application of Dyes, Plenum Press, New York, 1990, or M. Okawara, T. Kitao, T. Hirashima, M. Matsuoka, Organic Colorants, Elsevier, Amsterdam, 1988, or in the references cited therein.

The present invention also provides novel pyridone compounds of the formula II

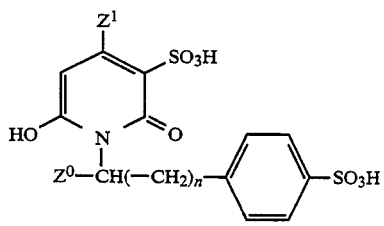 (II)

where
n is 1 or 2,
$Z^0$ is hydrogen or $C_1$–$C_4$-alkyl, and
$Z^1$ is hydrogen, $C_1$–$C_4$-alkyl or phenyl.

Preference is given to pyridone compounds of the formula II where n is 1, $Z^1$ is $C_1$–$C_4$-alkyl, in particular methyl, and $Z^0$ is hydrogen or methyl, in particular methyl.

Monosulfonic acids of a similar kind are known from DE-A-2,117,753.

The pyridone compounds II are highly suitable for use as coupling components for preparing azo dyes.

They can be obtained by reacting for example a hydroxypyridone of the formula VIII

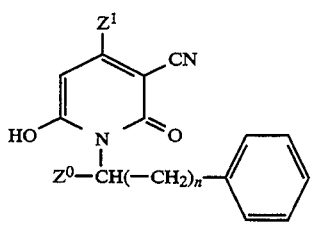 (VIII)

where n, $Z^0$ and $Z^1$ are each as defined above, in a baking process or with concentrated sulfuric acid in a two-stage reaction in a one-got process in the presence or absence of oleum. In general, the first stage is carried out at from 30° to 70° C. and the second at from 120° to 150° C.

It has also been found that the preparation of the pyridone compounds of the formula IIa

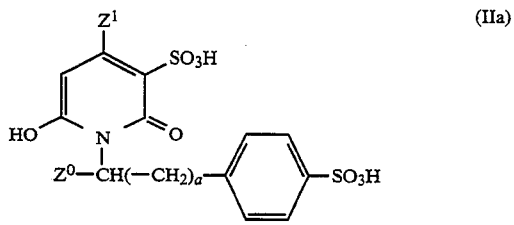 (IIa)

where
a is 0, 1 or 2,
$Z^0$ is hydrogen or $C_1$–$C_4$-alkyl and
$Z^1$ is hydrogen, $C_1$–$C_4$-alkyl or phenyl, by reaction of pyridones of the formula IIb

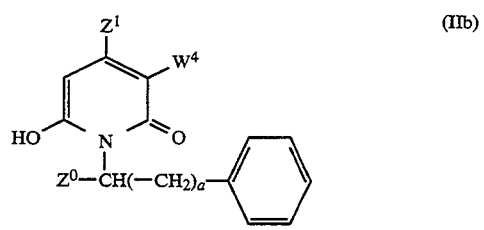 (IIb)

where $W^4$ is cyano or acetyl and a, $Z^0$ and $Z^1$ are each as defined above, with oleum is particularly successful on using oleum which contains from 1 to 2 mol of free sulfur trioxide and carrying out the reaction in a first stage at from 0° to 75° C. for from 1 to 5 hours and then in a second stage at from 80° to 135° C. for from 2 to 11 hours.

In this process, the sulfonic acid group goes into the phenyl ring in the first stage and into the pyridine ring in the second stage.

The reaction mixture is worked up in a conventional manner, for example by stirring out onto ice-water and subsequent neutralization, for example with sodium hydroxide solution.

The oleum used is advantageously a product which contains from 1 to 2 mol, preferably from 1 to 1.5 mol, of free sulfur trioxide.

The molar ratio of oleum:pyridone IIb is in general from 0.5:1 to 0.55:1, preferably from about 0.51:1.

It is also possible to use more oleum or oleum having a higher sulfur trioxide content, but this does not yield any further benefits. On the contrary, distinctly more ice-water and sodium hydroxide solution is required in the subsequent working up of the reaction mixture.

The novel benzophenoneazo dyes of the formula I are advantageously suitable for dyeing natural or synthetic substrates, for example wool, leather or polyamide. The dyes obtained have good general use fastness properties.

They are also suitable for the ink jet process.

The following Examples further illustrate the invention:

EXAMPLE 1

21.2 g of the diazo component of the formula

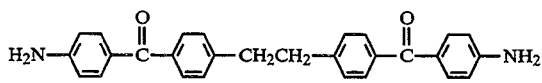

were suspended with 60 ml of concentrated hydrochloric acid, 60 ml of glacial acetic acid and 0.2 g of an acidic wetting agent. The mixture was then cooled down to 0° C., and 31 ml of 23% strength by weight aqueous sodium nitrite solution were added at from 0° to 6° C. Presently a clear diazonium salt solution was obtained, which was subsequently stirred at from 0° to 6° C. for 2 hours. Excess nitrous acid was then destroyed with sulfamic acid. Then this mixture was mixed with 35.6 g of the coupling component of the formula

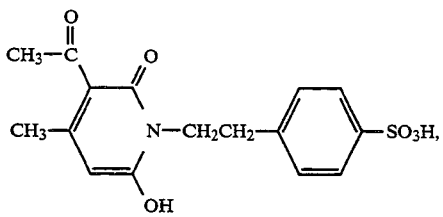

which had beforehand been dissolved in 250 ml of water with 26 g of 50% strength by weight sodium hydroxide solution and cooled down to 0° C.

The coupling mixture was buffered at from 0° to 6° C. with sodium hydroxide solution at a pH of 3.5–4. The resulting dye of the formula

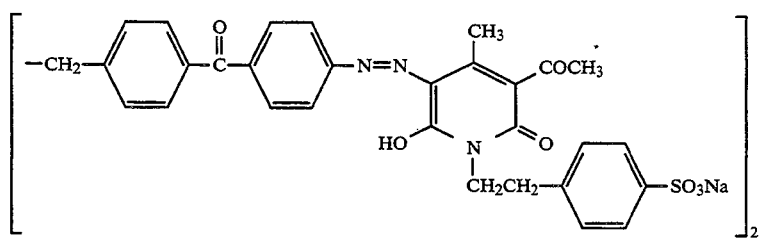

was precipitated with sodium chloride, filtered off with suction, dried and ground. 120 g were obtained of a yellow powder having a dye content of 50% by weight.

The absorption maximum of a dye solution in a mixture of 1 g of glacial acetic acid and 9 g of N,N-dimethylformamide is 428 nm.

The dye produces dyeings on leather, nylon and wool in a bright yellow shade of good and wet and light fastness.

EXAMPLE 2

Example 1 was repeated, except that the coupling component was replaced by 35.7 g of the coupling component of the formula

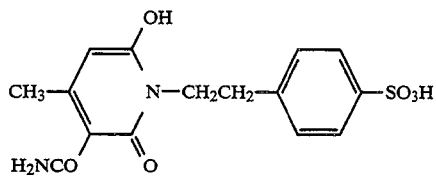

affording 59.5 g of the dye of the formula

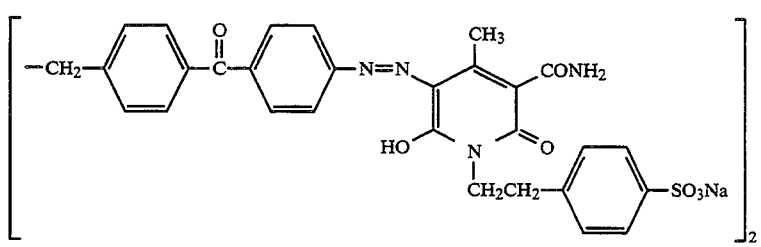

as a 50% strength by weight yellow powder whose absorption maximum in a solution of 9:1 g/g N,N-dimethylformamide/glacial acetic acid is 429 nm.

The dye gives deep bright yellow dyeings on wool and nylon having good fastness properties.

EXAMPLE 3

Example 1 was repeated, except that the coupling component was replaced by 20.5 g of the coupling component of the formula

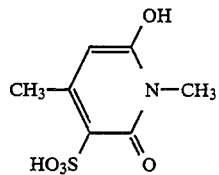

affording 42 g of the dye of the formula

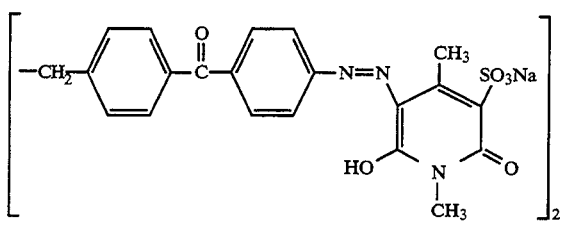

as a 90% strength by weight powder.

The dye produces bright yellow dyeings on nylon, wool and leather of good light fastness.

The ink jet process gives prints having good general use fastness properties.

The absorption maximum in water is 420 nm.

EXAMPLE 7

30.7 g of the diazo component 4-amino-4'-methoxybenzophenone-3'-sulfonic acid were diazotized as described in Example 6. The resulting suspension of the diazonium salt was admixed with 17.3 g of 1-phenyl-3-methyl-5-aminopyrazole, dissolved in 150 ml of water with 9 ml of concentrated hydrochloric acid. The pH of the reaction mixture was then gradually raised to 2.6–3.5 and subsequently stirred at pH 3–3.5 for 2 hours. The dye of the formula The dye has high affinity for nylon and wool and levels out differences in material in particular in the case of nylon. Its migration and light fastness properties on nylon are good. Nylon and wool are dyed a greenish yellow.

EXAMPLE 8

29.1 g of 4-amino-4'-methylbenzophenone-3'-sulfonic acid were diazotized as described in Example 6. After excess nitrous acid had been destroyed, the suspension of the diazonium salt was combined with a freshly prepared fine suspension of 31.9 g of 1-hydroxy-8-aminonaphthalene-3,6-disulfonic acid which was acidified with hydrochloric acid to pH 0.5–0. The reaction mixture was left to stir overnight at 5°–10° C., producing a red dye of the formula

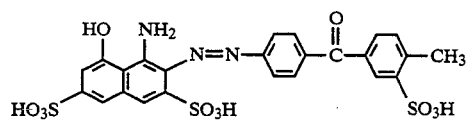

$\lambda_{max}$ (water): 601 nm

The dye was precipitated in full with sodium chloride and isolated in a conventional manner. The product thus isolated was dissolved with sodium hydroxide solution in 1000 ml of water at pH 6–9. The solution was then admixed with 0.1 mol of diazotized 4-amino-2',5'-dimethylbenzophenone, and the pH of the reaction mixture was maintained at >6–8. The resulting dye of the formula

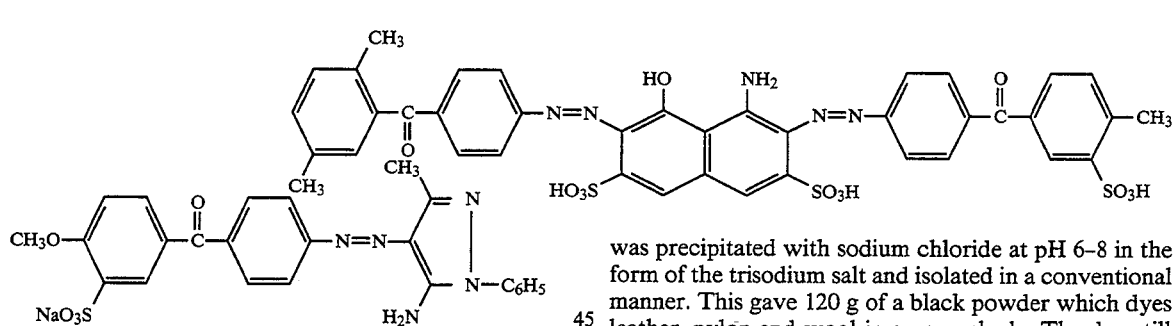

was salted out with sodium chloride and isolated, dried and ground in a conventional manner. This gave 51.2 g of the dye in the form of a 75% strength by weight yellow powder.

was precipitated with sodium chloride at pH 6–8 in the form of the trisodium salt and isolated in a conventional manner. This gave 120 g of a black powder which dyes leather, nylon and wool in a navy shade. The dye still contains about 24 g of sodium chloride.

The absorption maximum of the dye in water is 604 nm.

The same method was used to obtain the dyes listed below.

TABLE 1

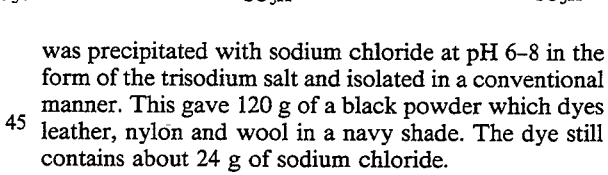

| Example No. | K | E | G | Hue | $\lambda_{max}$ [nm] |
|---|---|---|---|---|---|
| 9 | 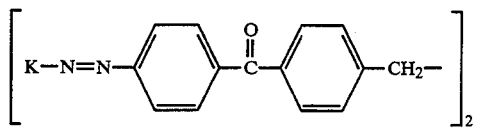 | CONH$_2$ | CH$_2$ | bright yellow | |

TABLE 1-continued $$\left[ K-N=N-\underset{\phantom{x}}{\overset{\displaystyle \bigcirc}{\underset{\phantom{x}}{\bigcirc}}}-\underset{\phantom{x}}{\overset{O}{\underset{\phantom{x}}{\|}}}-\underset{\phantom{x}}{\bigcirc}-CH_2- \right]_2$$

| # | K | E | G | Color |
|---|---|---|---|---|
| 10 | 4-methyl-3-(substituent E)-6-hydroxy-1-(N-G-phenyl-4-SO₃H)-pyridin-2-one | COCH₃ | CH₂ | bright yellow |
| 11 | 4-methyl-3-(substituent E)-6-hydroxy-1-(N-G-phenyl-4-SO₃H)-pyridin-2-one | COCH₃ | CH₂—CH(CH₃) | bright yellow |
| 12 | 4-methyl-3-(substituent E)-6-hydroxy-1-(N-G-phenyl-4-SO₃H)-pyridin-2-one | COCH₃ | CH₂CH₂CH₂ | bright yellow |
| 13 | 4-methyl-3-(substituent E)-6-hydroxy-1-(N-G-phenyl-4-SO₃H)-pyridin-2-one | CONH₂ | CH(CH₃)CH₂ | bright yellow |
| 14 | 4,6-dimethyl-2-(N-G)-amino-pyrimidine with NH-E | — | CH₂—CH₂—C₆H₄-SO₃H | C₂H₅ | yellow |
| 15 | 3-E-4-methyl-5-amino-pyrazole (N-G) | CH₃ | C₆H₄-SO₃H (4-) | greenish yellow |
| 16 | 3-E-4-methyl-5-amino-pyrazole (N-G) | H | CH₂-C₆H₄-SO₃H (4-) | greenish yellow |
| 17 | 4-hydroxy-3-methyl-naphthalene-1-CO₃H | — | — | yellowish |

TABLE 1-continued $$\left[ K-N=N-\underset{\underset{O}{\|}}{\overset{}{\bigcirc}}-\overset{}{\underset{}{C}}-\underset{}{\bigcirc}-CH_2- \right]_2$$

| No. | K | Hue | |
|---|---|---|---|
| 18 | 8-hydroxy-1-methyl-2-amino-6-sulfonaphthalene | red | 509 (in water) |
| 19 | 4,6-dimethyl-2-[(3-methoxypropyl)amino]pyrimidine linked to phenyl-SO₃H | yellow | |

| Example No. | K | $R^1$ | $R^2$ | $R^3$ | $G^1$ | $G^2$ | Hue |
|---|---|---|---|---|---|---|---|
| 20 | 4,6-dimethyl-2-NHG¹-pyrimidine with NHG² | H | $CH_3$ | H | 2,5-dimethyl-phenyl-SO₃H | $C_4H_9(n)$ | yellow |
| 21 | 4,6-dimethyl-2-NHG¹-pyrimidine with NHG² | $CH_3$ | $CH_3$ | H | 3-sulfophenyl | $C_4H_9(n)$ | yellow |
| 22 | 4,6-dimethyl-2-NHG¹-pyrimidine with NHG² | $CH_3$ | H | $CH_3$ | 4-sulfophenyl | $C_4H_9(n)$ | yellow |
| 23 | pyrazole with G¹, G², NH₂ | H | $CH_3$ | H | H | $CH_2$-phenyl-$SO_3H$ | yellow |
| 24 | pyrazole with G¹, G², NH₂ | $CH_3$ | $CH_3$ | H | H | $CH_2$-phenyl-$SO_3H$ | yellow |
| 25 | pyrazole with G¹, G², NH₂ | $CH_3$ | $CH_3$ | H | $CH_3$ | 4-sulfophenyl | yellow |

TABLE 1-continued $$\left[ K-N=N-\underset{}{\underset{}{\bigcirc}}-\overset{O}{\underset{\parallel}{C}}-\underset{}{\underset{}{\bigcirc}}-CH_2- \right]_2$$

| No. | K | | | | | Color |
|---|---|---|---|---|---|---|
| 26 | 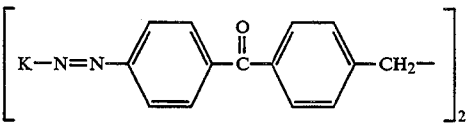 (G¹-C(=N-N(-G²)-)-C(CH₃)=C(NH₂)-) | H | Cl | H | CH₃ | C₆H₅ | yellow |
| 27 | 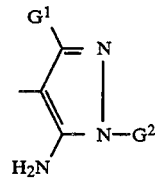 (2,5-di-G-4-aminophenyl) | H | OCH₃ | H | OCH₃ | OCH₃ | orange |
| 28 | 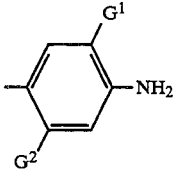 | H | OCH₃ | H | OCH₃ | OCH₃ | orange |
| 29 | 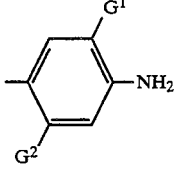 | H | OCH₃ | H | CH₃ | CH₃ | orange |

TABLE 2

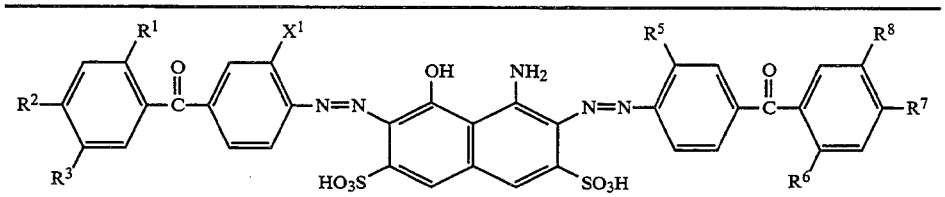

| Example No. | R¹ | R² | R³ | X¹ | R⁵ | R⁶ | R⁷ | R⁸ |
|---|---|---|---|---|---|---|---|---|
| 30 | H | CH₃ | CH₃ | H | SO₃H | H | OCH₃ | H |
| 31 | CH₃ | CH₃ | H | H | SO₃H | H | OCH₃ | H |
| 32 | H | CH₃ | CH₃ | H | SO₃H | H | CH₃ | H |
| 33 | H | CH₃ | H | H | SO₃H | H | CH₃ | H |
| 34 | H | CH₃ | CH₃ | H | H | H | OCH₃ | SO₃H |
| 35 | CH₃ | CH₃ | H | H | H | H | OCH₃ | SO₃H |
| 36 | H | CH₃ | CH₃ | H | H | H | CH₃ | SO₃H |
| 37 | H | CH₃ | H | H | H | H | CH₃ | SO₃H |
| 38 | OCH₃ | H | CH₃ | H | H | CH₃ | CH₃ | SO₃H |
| 39 | H | CH₃ | H | SO₃H | H | OCH₃ | CH₃ | H |
| 40 | H | OCH₃ | H | SO₃H | H | H | OCH₃ | H |
| 41 | H | C₂H₅ | H | H | SO₃H | H | C₂H₅ | H |
| 42 | H | C₂H₅ | H | H | H | H | C₂H₅ | SO₃H |
| 43 | CH₃ | CH₃ | H | H | H | H | CH₃ | SO₃H |
| 44 | H | Cl | H | H | H | H | CH₃ | SO₃H |
| 45 | H | C₂H₅ | H | H | H | H | CH₃ | SO₃H |

TABLE 3
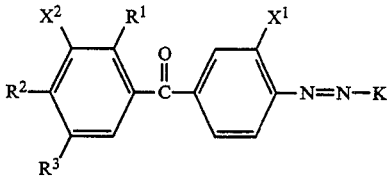
| Example No. | $R^1$ | $R^2$ | $R^3$ | $X^1$ | $X^2$ | K | Hue |
|---|---|---|---|---|---|---|---|
| 46 | H | $CH_3$ | H | $SO_3H$ | H | 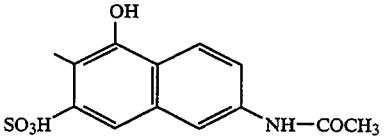 | orange |
| 47 | H | $CH_3$ | $CH_3$ | $SO_3H$ | H | 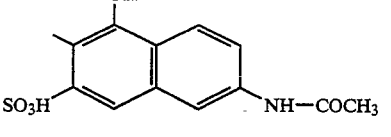 | orange |
| 48 | H | $CH_3$ | $CH_3$ | H | $SO_3H$ | 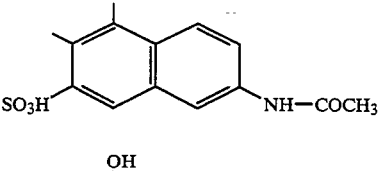 | orange |
| 49 | $CH_3$ | $CH_3$ | H | $SO_3H$ | H | 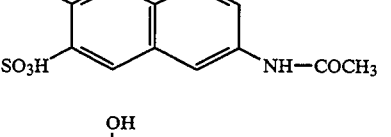 | orange |
| 50 | H | $OCH_3$ | H | $SO_3H$ | H | 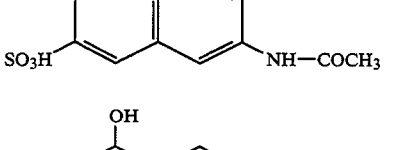 | orange |
| 51 | H | $C_2H_5$ | H | $SO_3H$ | H | 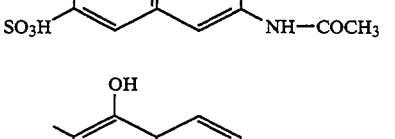 | orange |
| 52 | H | Cl | H | $SO_3H$ | H | 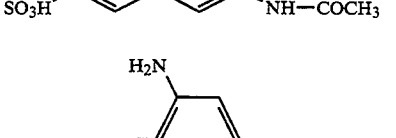 | orange |
| 53 | H | $C_2H_5$ | H | $SO_3H$ | H | 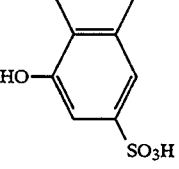 | red |

TABLE 3-continued
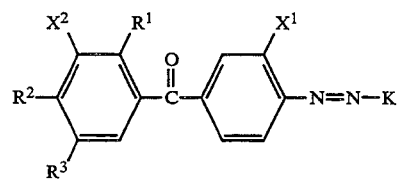
| Example No. | R[1] | R[2] | R[3] | X[1] | X[2] | K | Hue |
|---|---|---|---|---|---|---|---|
| 54 | H | CH$_3$ | H | SO$_3$H | H | 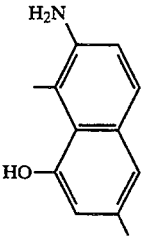 | red |
| 55 | H | OCH$_3$ | H | SO$_3$H | H | 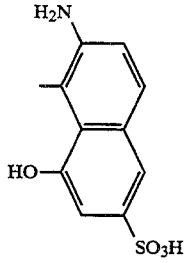 | red |
| 56 | H | OCH$_3$ | SO$_3$H | H | H | 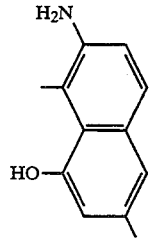 | red |
| 57 | H | C$_2$H$_5$ | SO$_3$H | H | H | 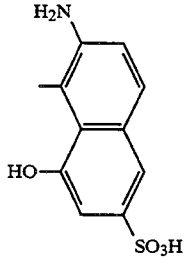 | red |
| 58 | H | CH$_3$ | SO$_3$H | SO$_3$H | H | 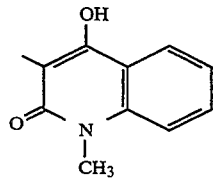 | yellow |

TABLE 4

Structure: naphthalene with OH, NH₂, two SO₃H groups and two azo linkages to G¹ and G²:

$G^2-N=N-$ [naphthalene with OH, NH₂, HO₃S, SO₃H] $-N=N-G^1$

| Example No. | G¹ | G² | Hue |
|---|---|---|---|
| 59 | 4-(3-sulfo-4-methylbenzoyl)phenyl- (benzoyl group with SO₃H and CH₃) | phenyl-SO₂-O-(3-methylphenyl) | blue |
| 60 | 4-methyl-2-sulfophenyl- | 4-methylphenyl-CO-4-methylphenyl (4,4'-dimethylbenzophenone) | blue |
| 61 | 3-sulfo-4-methylphenyl- | 4-ethylphenyl-CO-4-methylphenyl | blue |
| 62 | 2,4-dimethyl-5-sulfophenyl- | 4-methoxyphenyl-CO-4-methylphenyl | blue |
| 63 | 2-(4-methylphenyl)-6-methyl-7-sulfo-benzothiazol-yl | 4-methoxyphenyl-CO-4-methylphenyl | bluish black |
| 64 | 4-(SO₂CH₂CH₂OSO₃H)phenyl- | 4-ethylphenyl-CO-4-methylphenyl | bluish black |

TABLE 5

Structure:

R²,R¹-substituted phenyl—C(=O)—(X¹,X²,Cl-substituted phenyl)—N=N—K with R³ and additional substituents as shown

| Example No. | K | X¹ | R¹ | R² | R³ | X² | Hue or λ_max [nm] |
|---|---|---|---|---|---|---|---|
| 65 | 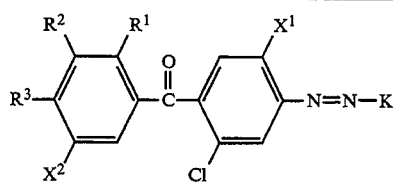 | H | H | CH₃ | OCH₃ | SO₃H | yellow |
| 66 | | H | H | H | OCH₃ | SO₃H | yellow |
| 67 | | H | H | H | OCH₃ | SO₃H | yellow |
| 68 | | SO₃H | H | H | OCH₃ | H | yellow |

K = pyrazole derivative with CH₃, N=N, N—C₆H₅, H₂N substituents

TABLE 5-continued

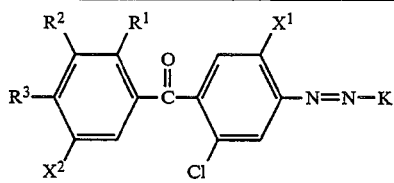

| Example No. | K | $X^1$ | $R^1$ | $R^2$ | $R^3$ | $X^2$ | Hue or $\lambda_{max}$ [nm] |
|---|---|---|---|---|---|---|---|
| 69 | | $SO_3H$ | H | H | $OCH_3$ | H | greenish yellow |
| 70 | | $SO_3H$ | H | H | $OCH_3$ | H | greenish yellow |
| 71 | | $SO_3H$ | $CH_3$ | H | H | $CH_3$ | greenish yellow |
| 72 | | $SO_3H$ | H | H | $CH_3$ | H | greenish yellow |
| 73 | | H | $CH_3$ | H | $CH_3$ | $SO_3H$ | greenish yellow |
| 74 | | H | H | H | $C_2H_5$ | $SO_3H$ | greenish yellow |
| 75 | | H | H | H | $CH_3$ | H | greenish yellow |
| 76 | | $SO_3H$ | H | H | $OCH_3$ | H | greenish yellow |
| 77 | | $SO_3H$ | H | H | $C_2H_5$ | H | greenish yellow |
| 78 | | $SO_3H$ | H | H | $CH(CH_3)_2$ | H | greenish yellow |
| 79 | | H | H | H | $C_2H_5$ | $SO_3H$ | greenish yellow |
| 80 | | $SO_3H$ | H | $CH_3$ | $CH_3$ | H | yellowish red |
| 81 | | $SO_3H$ | H | H | $C_2H_5$ | H | yellowish red |
| 82 | | $SO_3H$ | H | H | $CH(CH_3)_2$ | H | yellowish red |
| 83 | | $SO_3H$ | H | H | $C_3H_7(i)$ | H | orange |
| 84 | | $SO_3H$ | H | $CH_3$ | $CH_3$ | H | orange |
| 85 | | $SO_3H$ | H | H | $C_2H_5$ | H | orange |
| 86 | | $SO_3H$ | $CH_3$ | H | $CH_3$ | H | orange |
| 87 | | $SO_3H$ | H | H | $C_3H_7(i)$ | H | 403 |
| 88 | | $SO_3H$ | H | $CH_3$ | $CH_3$ | H | 404 |
| 89 | | $SO_3H$ | H | H | $C_2H_5$ | H | orange |
| 90 | | $SO_3H$ | $CH_3$ | H | $CH_3$ | H | orange |

TABLE 5-continued

| Example No. | K | $X^1$ | $R^1$ | $R^2$ | $R^3$ | $X^2$ | Hue or $\lambda_{max}$ [nm] |
|---|---|---|---|---|---|---|---|
| 91 | (N-ethyl-N-benzylsulfonate aniline) | $SO_3H$ | H | H | $CH_3$ | H | yellowish red |
| 92 | | $SO_3H$ | $CH_3$ | H | $CH_3$ | H | yellowish red |
| 93 | | $SO_3H$ | H | H | $C_2H_5$ | H | yellowish red |
| 94 | (N-ethyl-N-(sulfophenethyl) acetamidoaniline) | $SO_3H$ | H | H | $CH_3$ | H | red |
| 95 | | $SO_3H$ | H | H | $OCH_3$ | H | red |
| 96 | | $SO_3H$ | $CH_3$ | H | H | $CH_3$ | red |
| 97 | (bis-hydroxyethylamino pyrimidine) | $SO_3H$ | H | H | $OCH_3$ | H | orange |
| 98 | | $SO_3H$ | H | H | $CH_3$ | H | orange |

TABLE 6

| Ex. No. | $X^1$ | $R^1$ | $R^2$ | $R^3$ | $R^5$ | $R^4$ | G | Hue or $\lambda_{max}$ [nm] |
|---|---|---|---|---|---|---|---|---|
| 99 | H | H | H | $CH_3$ | H | H | $CH_3$ | 421 |
| 100 | H | H | H | $C_2H_5$ | H | H | $CH_3$ | 421 |
| 101 | H | H | $CH_3$ | $CH_3$ | H | H | $CH_3$ | 422 |
| 102 | H | $CH_3$ | H | $CH_3$ | H | H | $CH_3$ | 420 |
| 103 | H | $OCH_3$ | H | H | $CH_3$ | H | $CH_3$ | 422 |
| 104 | H | $CH_3$ | H | $OCH_3$ | H | H | $C_2H_5$ | 423 |
| 105 | H | H | H | $CH_3$ | H | Cl | $CH_3$ | 421 |
| 106 | H | H | H | $C_2H_5$ | H | Cl | $CH_3$ | 421 |
| 107 | H | H | H | $OCH_3$ | H | Cl | $CH_3$ | 422 |
| 108 | $SO_3H$ | H | $CH_3$ | $CH_3$ | H | H | $C_2H_5$ | |
| 109 | $SO_3H$ | $CH_3$ | H | $CH_3$ | H | H | $C_2H_5$ | |
| 110 | $SO_3H$ | H | H | $C_2H_5$ | H | H | $CH_3$ | |
| 111 | $SO_3H$ | H | H | $C_2H_5$ | H | Cl | $CH_3$ | |
| 112 | H | H | H | $C_2H_5$ | $SO_3H$ | H | $CH_3$ | 421 |
| 113 | H | H | H | $C_2H_5$ | $SO_3H$ | Cl | $CH_3$ | 421 |
| 114 | H | H | $CH_3$ | $CH_3$ | $SO_3H$ | H | $CH_3$ | 421 |
| 115 | H | H | $CH_3$ | $CH_3$ | $SO_3H$ | H | $C_4H_9(n)$ | 421 |
| 116 | H | H | $CH_3$ | $OCH_3$ | H | Cl | $CH_3$ | 422 |
| 117 | $SO_3H$ | H | $CH_3$ | $CH_3$ | H | $OCH_3$ | $CH_3$ | |
| 118 | H | H | H | $CH_3$ | H | $OCH_3$ | $CH_3$ | |

EXAMPLE 119
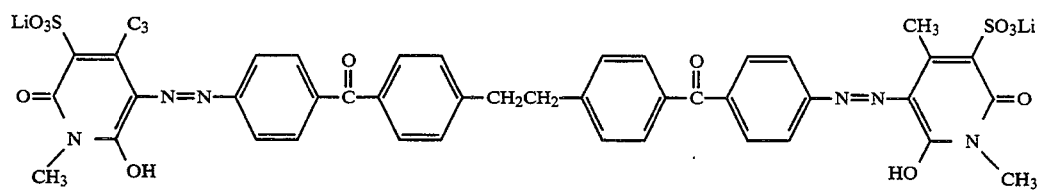
Brilliant greenish yellow on leather, nylon and wool.
EXAMPLE 120
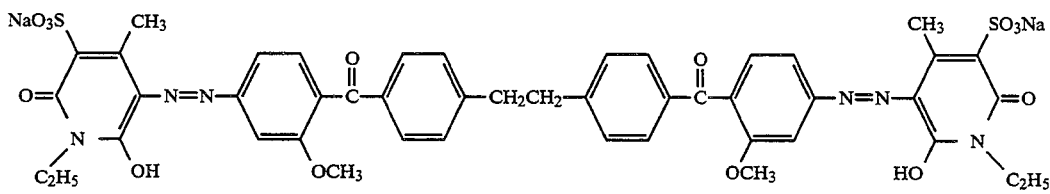
Bright greenish yellow on leather, nylon and wool.
EXAMPLE 121
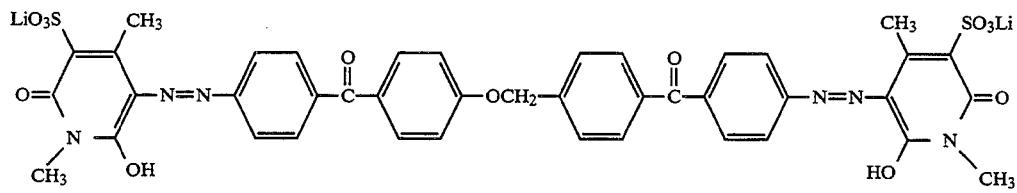
Greenish yellow on leather, nylon and wool.
EXAMPLE 122
Greenish yellow on nylon, wool and leather.
EXAMPLE 123
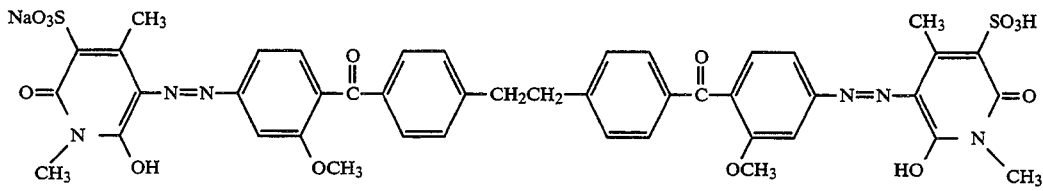
Greenish yellow on leather and wool.
EXAMPLE 124
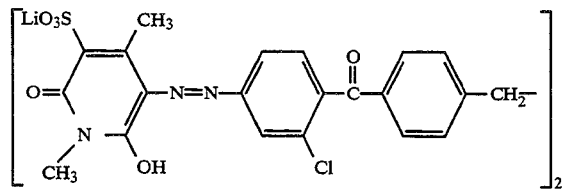
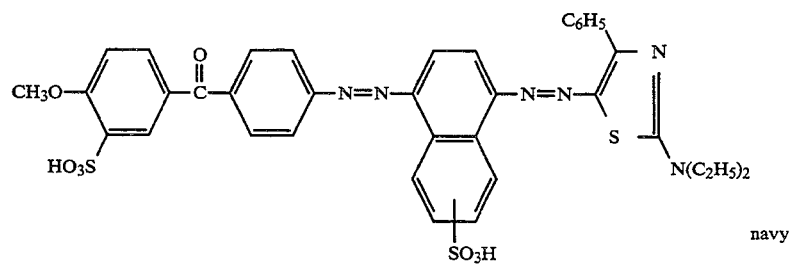
navy

EXAMPLE 125
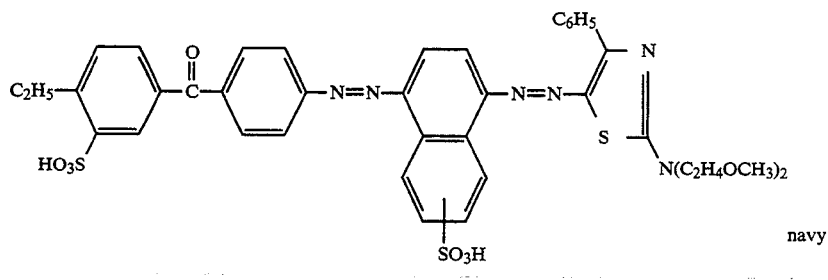
EXAMPLE 126
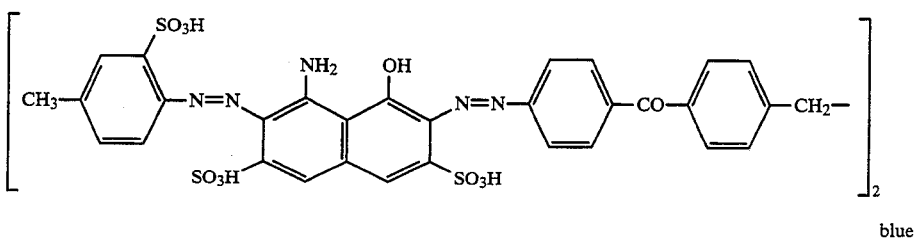
blue
EXAMPLE 127
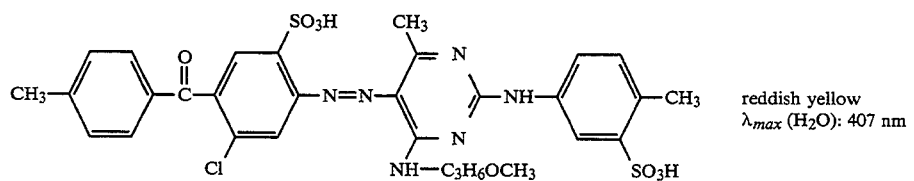
reddish yellow
$\lambda_{max}$ (H₂O): 407 nm
EXAMPLE 128
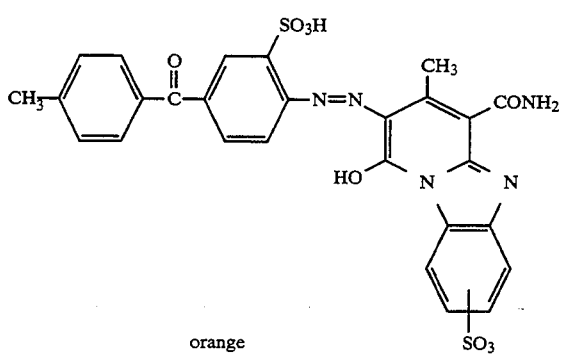
orange
EXAMPLE 129
navy
EXAMPLE 129 (cont.)
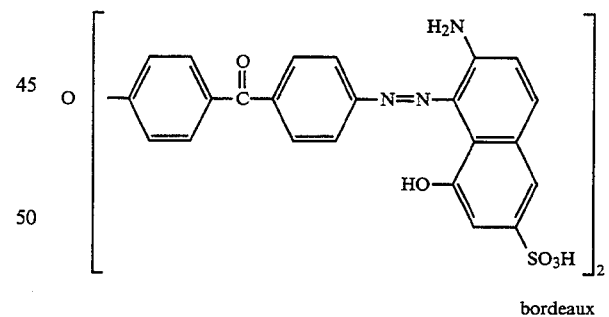
bordeaux
EXAMPLE 130
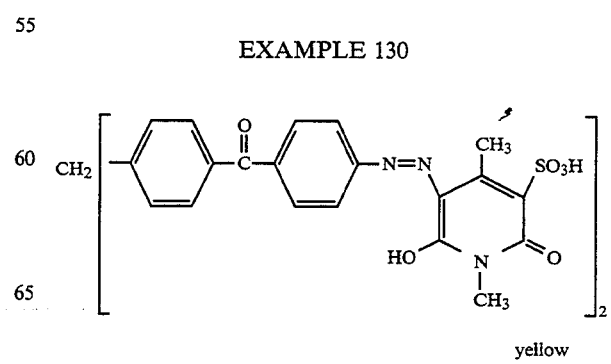
yellow

EXAMPLE 131

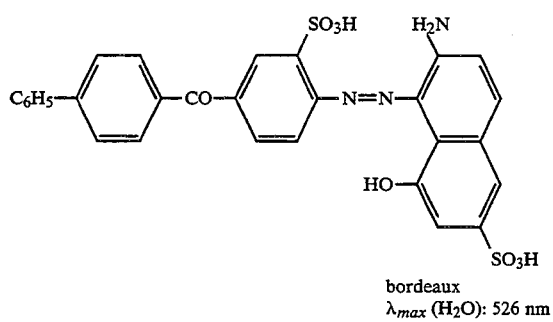

bordeaux
$\lambda_{max}$ (H₂O): 526 nm

EXAMPLE 132

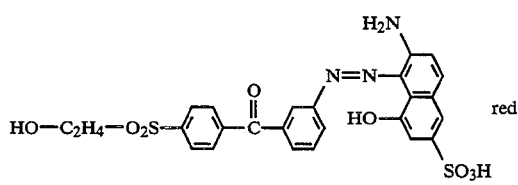

red

TABLE 7

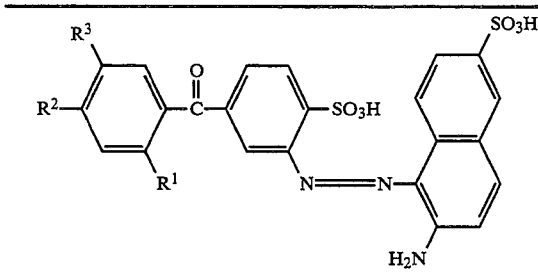

| Example No. | R¹ | R² | R³ | Hue | $\lambda_{max}$ (H₂O) [nm] |
|---|---|---|---|---|---|
| 133 | H | CH₃ | H | bright red | 509 |
| 134 | H | C₂H₅ | H | bright red | 509 |
| 135 | H | CH(CH₃)₂ | H | bright red | 508 |

TABLE 7-continued

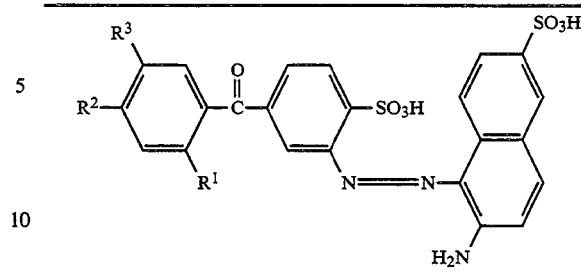

| Example No. | R¹ | R² | R³ | Hue | $\lambda_{max}$ (H₂O) [nm] |
|---|---|---|---|---|---|
| 136 | CH₃ | CH₃ | H | bright red | 509 |
| 137 | CH₃ | H | CH₃ | bright red | 509 |
| 138 | H | CH₃ | CH₃ | bright red | 509 |
| 139 | H | C₆H₅ | H | bright red | 512 |
| 140 | H | Cl | H | bright red | 511 |
| 141 | H | CH₃ | Cl | bright red | 510 |

EXAMPLE 142 (use)

100 parts by weight of a retanned chrome leather having a shaved thickness of 1.4 mm were neutralized by drumming for 45 minutes in 200 parts by weight of water at 30° C. with 1 part by weight of sodium bicarbonate and 1 part by weight of sodium formate. The leather was then washed in 200 parts by weight of fresh water at 30° C. by drumming for 15 minutes. Thereafter the dyeing was effected by drumming for 45 minutes in 200 parts by weight of water at 50° C. containing 1% by weight of the dye described in Example 2. Then 4 parts by weight of a commercial fat liquor were added and drumming was continued for 30 minutes. After acidification with 0.5 part by weight of formic acid, the leather was drummed for a further 30 minutes and then rinsed with cold water, set out, dried, sawdusted, staked and strained.

The result obtained was leather dyed in a deep bright yellow shade having good light fastness and good wet fastness properties.

Similar results are obtained in the dyeing of leather with the dyes listed hereinafter.

TABLE 8

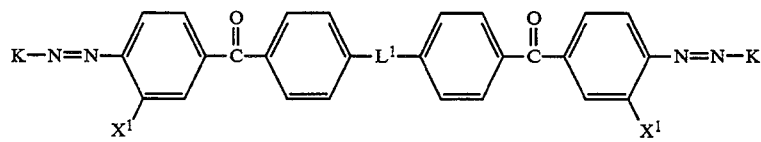

| Example No. | L¹ | X¹ | K | Hue |
|---|---|---|---|---|
| 143 | CH₂CH₂ | H | 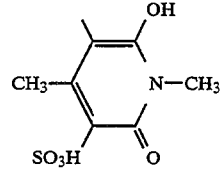 | greenish yellow |
| 144 | CH₂CH₂ | H | 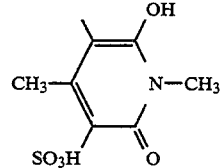 | greenish yellow |

TABLE 8-continued
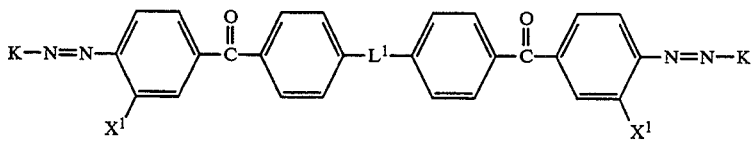
| Example No. | L¹ | X¹ | K | Hue |
|---|---|---|---|---|
| 145 | CH₂CH₂ | H | 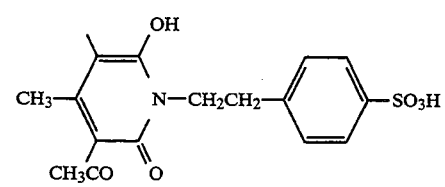 | greenish yellow |
| 146 | CH₂CH₂ | H | 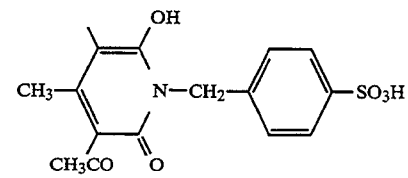 | greenish yellow |
| 147 | CH₂CH₂ | H | 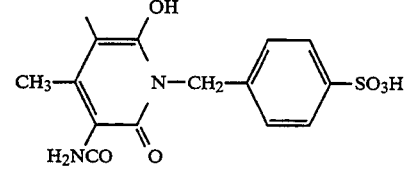 | greenish yellow |
| 148 | CH₂CH₂ | H | 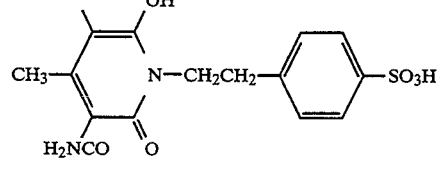 | greenish yellow |
| 149 | CH₂CH₂ | H | 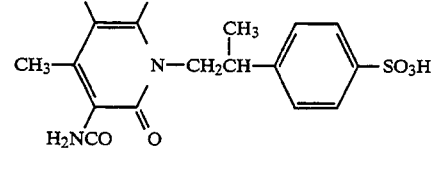 | greenish yellow |
| 150 | CH₂—O | H | 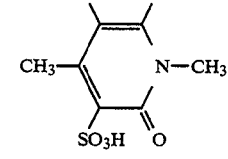 | greenish yellow |
| 151 | CH₂CH₂ | H | 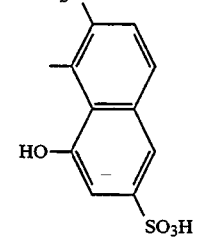 | bluish red $\lambda_{max}$ (H₂O): 529 nm |

TABLE 8-continued

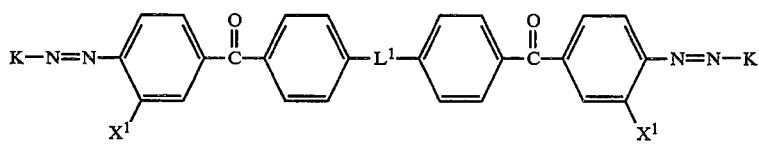

| Example No. | $L^1$ | $X^1$ | K | Hue |
|---|---|---|---|---|
| 152 | $CH_2CH_2$ | H | 4-OH, 2-CH_3, 1-SO_3H naphthalene (see structure) | orange |
| 153 | $CH_2CH_2$ | $SO_3H$ | pyridone: OH, CH_3, N—C_2H_5, H_2NCO, =O | greenish yellow |
| 154 | $CH_2CH_2$ | $SO_3H$ | pyridone: OH, CH_3, N—CH_3, CH_3CO, =O | greenish yellow |
| 155 | $CH_2CH_2$ | $SO_3H$ | pyridone: OH, CH_3, N—CH_2CH_2OCH_3, CH_3CO, =O | greenish yellow |

TABLE 9

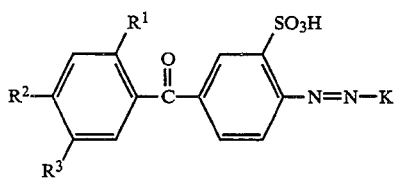

| Example No. | $R^1$ | $R^2$ | $R^3$ | K | Hue |
|---|---|---|---|---|---|
| 156 | H | $CH_3$ | H | pyrimidine with CH_3, NH—C_2H_5, NH-phenyl-SO_3H | reddish orange |
| 157 | H | $CH_3$ | H | pyrimidine with CH_3, NH—C_3H_6OCH_3, NH-phenyl-SO_3H | reddish orange |

TABLE 9-continued

| Example No. | R¹ | R² | R³ | K | Hue |
|---|---|---|---|---|---|
| 158 | H | $C_2H_5$ | H | (structure with $CH_3$, N, NH-phenyl-$SO_3H$, NH—$C_3H_6OCH_3$) | reddish orange |
| 159 | H | $CH_3$ | $CH_3$ | (structure with $CH_3$, N, NH-phenyl-$SO_3H$, NH—$C_3H_6OCH_3$) | reddish orange |
| 160 | $CH_3$ | $CH_3$ | H | (structure with $CH_3$, N, $N(C_4H_9)_2$, $HNCH_2CH_2$-phenyl-$SO_3H$) | orange |

EXAMPLE 161

42.1 g of the diazo component of the formula

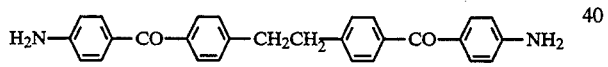

were stirred at room temperature with 90 ml of 25% strength by weight hydrochloric acid and 10 drops of a wetting agent effective under acid conditions. After 2 hours 100 g of ice were added and the suspension was admixed with a total of 64 ml of 23% strength by weight aqueous sodium nitrite solution while cooling was applied. The diazotization batch was subsequently stirred at from 0° to 8° C. for 2.5 hours. Excess nitrous acid was then completely destroyed with amidosulfuric acid and the diazonium salt solution obtained was diluted with 150 ml of ice-water. The mixture was then added to 65.1 g of the coupling component of the formula

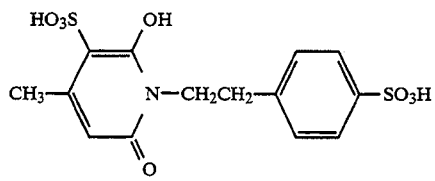

which had been dissolved at pH 7 in 300 ml of water and 300 ml of ice. During the addition of the diazonium salt solution the pH of the reaction mixture was maintained within the range from 4 to 7 by adding sodium hydroxide solution. The coupling did not take long. The honey yellow dye solution obtained was spray dried at a pH of from 4 to 6, giving 122 g of the dye of the formula

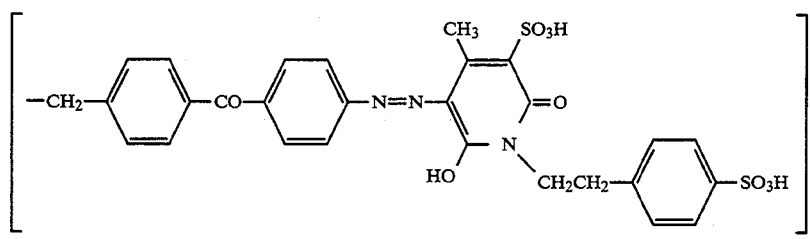

in the form of the sodium salt of the sulfonic acids. The yellow powder still contains sodium chloride.

From 0.5 to 1% strength dyeings with this dye on retanned leather are a bright, very good wet-fast and light-last greenish yellow. $\lambda_{max}$ ($H_2O$): 421 nm.

Replacing the abovementioned diazo component by a compound of the formula:
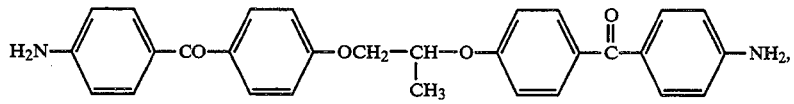
gives a yellow dye of the formula
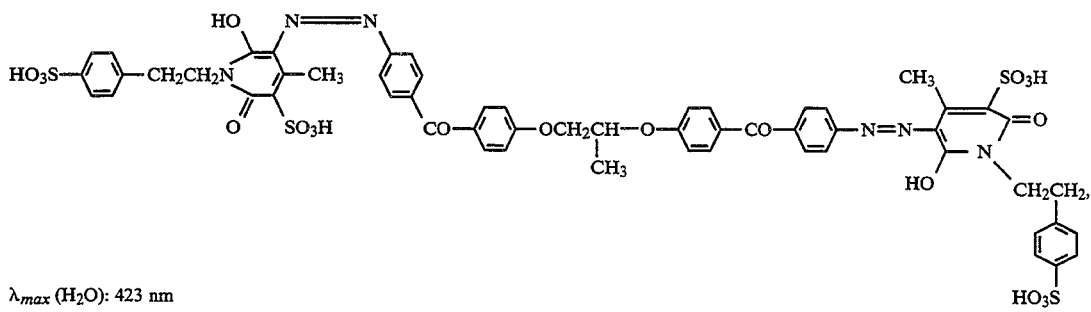
$\lambda_{max}$ (H$_2$O): 423 nm
which has a similar fastness profile.
The same method gives the following compounds and the dyes listed below in Tables 11 and 12.
EXAMPLE 162
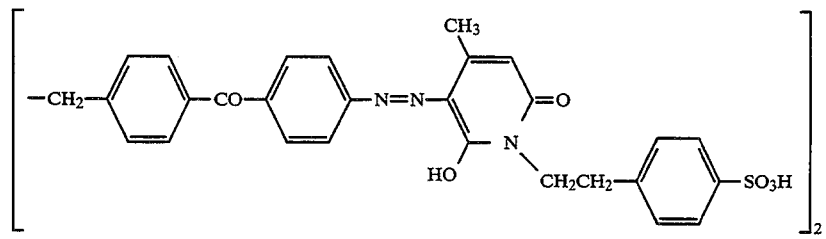
$\lambda_{max}$ (H$_2$O): 403 nm
EXAMPLE 163
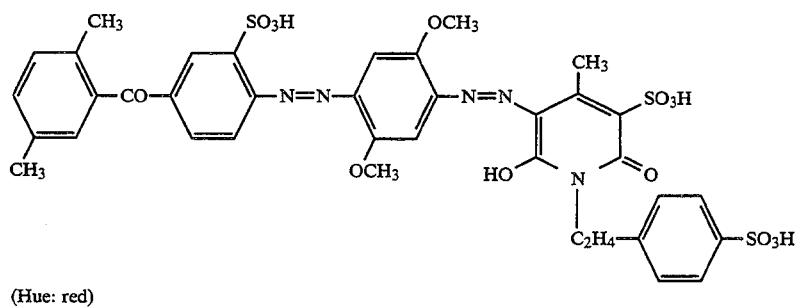
(Hue: red)

TABLE 10

Structure: Q¹-C(=O)-[phenyl]-N=N-[pyridone with CH₃, SO₃H, =O, OH, N-CH(Zº)-(CH₂)ₐ-[phenyl]-SO₃H]

| Ex. No. | Q¹ | Zº | a | λ$_{max}$ [nm] (in water) | Hue |
|---|---|---|---|---|---|
| 164 | 2,4-dimethylphenyl (CH₃, CH₃) | H | 1 | 431 | yellow |
| 165 | 2,4-diisopropylphenyl (CH(CH₃)₂, (CH₃)₂CH) | H | 1 | 431 | yellow |
| 166 | biphenyl-4-yl | H | 1 |  | yellow |
| 167 | 4-cyclohexylphenyl | H | 1 | 431 | yellow |
| 168 | naphthyl | H | 1 |  | yellow |
| 169 | acenaphthyl | H | 1 |  | yellow |
| 170 | C₆H₅— | H | 1 |  | greenish yellow |
| 171 | 4-CH₃-C₆H₄— | H | 1 | 431 | greenish yellow |
| 172 | 4-C₂H₅-C₆H₄— | H | 1 | 432 | greenish yellow |
| 173 | 4-(CH₃)₂CH-C₆H₄— | H | 1 | 432 | greenish yellow |

TABLE 10-continued

Structure:
$Q^1-\text{CO}-C_6H_4-N=N-$ [pyridone ring with CH$_3$, SO$_3$H, =O, HO, N-CH(Z$^o$)(-CH$_2$)$_a$-C$_6$H$_4$-SO$_3$H]

| Ex. No. | Q$^1$ | Z$^o$ | a | λ$_{max}$ [nm] (in water) | Hue |
|---|---|---|---|---|---|
| 174 | 4-Cl-C$_6$H$_4$- | H | 1 | 429 | greenish yellow |
| 175 | 2,4-(CH$_3$)$_2$-C$_6$H$_3$- | H | 0 | 430 | greehish yellow |
| 176 | 2,4-(CH$_3$)$_2$-C$_6$H$_3$- | CH$_3$ | 1 | 431 | greenish yellow |
| 177 | 2,4-(CH$_3$)$_2$-C$_6$H$_3$- | CH$_3$ | 2 | 431 | greenish yellow |
| 178 | 2,5-(CH$_3$)$_2$-C$_6$H$_3$- | H | 0 | 430 | greenish yellow |
| 179 | 2,5-(CH$_3$)$_2$-C$_6$H$_3$- | H | 1 | 430 | greenish yellow |
| 180 | 2,5-(CH$_3$)$_2$-C$_6$H$_3$- | CH$_3$ | 1 | 431 | greenish yellow |
| 181 | 4-(CH$_3$)$_2$CH-2-CH$_3$-C$_6$H$_3$- | H | 1 | 431 | greenish yellow |
| 182 | 4-Br-C$_6$H$_4$- | H | 1 | 430 | greenish yellow |

TABLE 10-continued

[Structure: Q¹-C(=O)-C₆H₄-N=N- attached to pyridone ring bearing CH₃, SO₃H, =O, HO-, and N-CH(Z°)-(CH₂)ₐ-C₆H₄-SO₃H]

| Ex. No. | Q¹ | Z° | a | λ_max [nm] (in water) | Hue |
|---|---|---|---|---|---|
| 183 | 4-chloro-2-methylphenyl | H | 1 | 430 | greenish yellow |
| 184 | 2-methyl-4-chlorophenyl (isomer) | H | 1 | 429 | greenish yellow |
| 185 | 3-chloro-4-methylphenyl | H | 1 | 430 | greenish yellow |
| 186 | 4-(2-phenylethyl)phenyl | H | 1 | 430 | greenish yellow |
| 187 | 4-methoxyphenyl | H | 1 | 432 | yellow |
| 188 | 4-ethoxyphenyl | H | 1 | 432 | yellow |
| 189 | 4-methoxy-2-methylphenyl | H | 1 | 432 | yellow |
| 190 | 3,5-dimethylphenyl | H | 1 | 431 | greenish yellow |
| 191 | 3,5-dimethylphenyl | CH₃ | 1 | 431 | greenish yellow |

TABLE 11

[Structure: naphthalene with H₂N, Q²-N=N-, HO, and SO₃H substituents]

| Ex. No. | Q² | λ_max [nm] (in water) | Hue |
|---------|----|-----------------------|-----|
| 192 | 2,4-dimethyl-5-sulfo-phenyl-CO-(4-chloro-3-methylphenyl) | | bluish red |
| 193 | 4-isopropyl-2-isopropyl-5-sulfo-phenyl-CO-(3-methylphenyl) | | bluish red |
| 194 | $C_7H_{15}(n)$—C₆H₄—CO—C₆H₃(3-CH₃)—SO₃H | 513 | bluish red |
| 195 | cyclohexyl—C₆H₄—CO—C₆H₃(3-CH₃)—SO₃H | 513 | bluish red |
| 196 | $C_9H_{19}(n)$—C₆H₄—CO—C₆H₃(3-CH₃)—SO₃H | 513 | bluish red |
| 197 | $C_{11}H_{23}(n)$—C₆H₄—CO—C₆H₃(3-CH₃)—SO₃H | 513 | bluish red |
| 198 | $C_9H_{19}(n)$—CH(CH₃)—C₆H₄—CO—C₆H₃(3-CH₃)—SO₃H | 513 | bluish red |
| 199 | $C_8H_{17}$—C₆H₃(2-CH₃)—CO—C₆H₃(3-CH₃)—SO₃H | 513 | bluish red |

TABLE 12

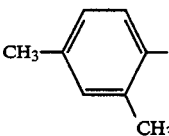

| Ex. No. | Q¹ | Q³ | Hue |
|---|---|---|---|
| 200 | 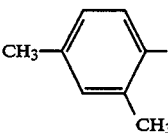 2,4-dimethylphenyl | CH₂ | greenish yellow |
| 201 | 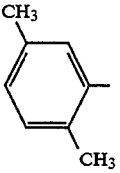 2,4-dimethylphenyl | C₂H₄ | greenish yellow |
| 202 | 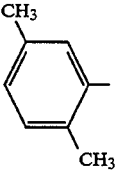 3,4-dimethylphenyl | CH₂ | greenish yellow |
| 203 | 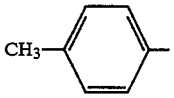 3,4-dimethylphenyl | C₂H₄ | greenish yellow |

EXAMPLE 204

257 g of 1-(2-phenylethyl)-6-hydroxy-3-cyano-4-methypyrid-2-one were introduced at not more than 70° C. into a mixture of 160 g of 100% strength by weight sulfuric acid and 380 g of oleum (24% strength by weight). The resulting solution was subsequently stirred at 75° C. for 5 hours to form essentially a product of the formula

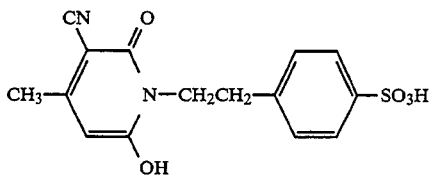

This was followed by heating over 5 hours to 110° C. to hydrolyze the cyano group and decarboxylate the carboxylic acid intermediate (foaming due to $CO_2$ evolution). Then the mixture was heated to 130°–135° C. and stirred at that temperature for 5.5 hours. After the reaction mixture had been cooled down to about 110° C., it was stirred into about 900 g of ice-water and the compound of the formula

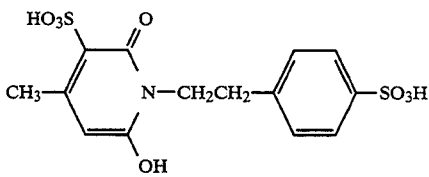

was neutralized at $\leq 30°$ C. with sodium hydroxide solution. This solution can be used directly for preparing azo dyes. $\lambda_{max}$ ($H_2O$): 325 nm, 247 nm (minimum at 280 and 235 nm).

TABLE 13

| Example No. | Q¹ | Z⁰ | a | $\lambda_{max}$ [nm] (in water) | Hue |
|---|---|---|---|---|---|
| 205 | C₆H₅— | H | 1 | | greenish yellow |
| 206 | 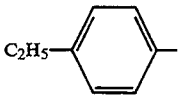 CH₃—C₆H₄— | H | 1 | 431 | greenish yellow |
| 207 | 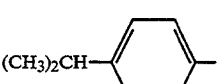 C₂H₅—C₆H₄— | H | 1 | 432 | greenish yellow |
| 208 | (CH₃)₂CH—C₆H₄— | H | 1 | 432 | greenish yellow |
| 209 | 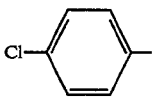 Cl—C₆H₄— | H | 1 | 429 | greenish yellow |

TABLE 13-continued

| Example No. | Q¹ | Z⁰ | a | $\lambda_{max}$ [nm] (in water) | Hue |
|---|---|---|---|---|---|
| 210 | 2,4-dimethylphenyl (CH₃ at 2, CH₃ at 4) | H | 0 | 430 | greenish yellow |
| 211 | 2,4-dimethylphenyl | CH₃ | 1 | 431 | greenish yellow |
| 212 | 2,4-dimethylphenyl | CH₃ | 2 | 431 | greenish yellow |
| 213 | 2,5-dimethylphenyl (CH₃ at 2, CH₃ at 5) | H | 0 | 430 | greenish yellow |
| 214 | 2,5-dimethylphenyl | H | 1 | 430 | greenish yellow |
| 215 | 2,5-dimethylphenyl | CH₃ | 1 | 431 | greenish yellow |
| 216 | 2-methyl-4-isopropylphenyl | H | 1 | 431 | greenish yellow |
| 217 | 4-bromophenyl | H | 1 | 430 | greenish yellow |
| 218 | 4-chloro-2-methylphenyl | H | 1 | 430 | greenish yellow |
| 219 | 2-methyl-4-chlorophenyl | H | 1 | 429 | greenish yellow |

TABLE 13-continued
| Example No. | Q¹ | Z° | a | $\lambda_{max}$ [nm] (in water) | Hue |
|---|---|---|---|---|---|
| 220 | 3-Cl-4-CH₃-phenyl | H | 1 | 430 | greenish yellow |
| 221 | 4-(2-phenylethyl)phenyl | H | 1 | 430 | greenish yellow |
| 222 | 4-CH₃O-phenyl | H | 1 | 432 | yellow |
| 223 | 4-C₂H₅O-phenyl | H | 1 | 432 | yellow |
| 224 | 4-CH₃O-2-CH₃-phenyl | H | 1 | 432 | yellow |
| 225 | 3,5-(CH₃)₂-phenyl | H | 1 | 431 | greenish yellow |
| 226 | 3,5-(CH₃)₂-phenyl | CH₃ | 1 | 431 | greenish yellow |
TABLE 14
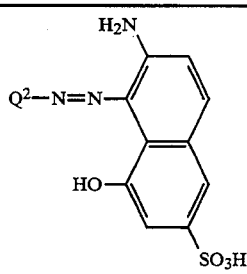
| Example No. | Q² | $\lambda_{max}$ [nm] (in water) | Hue |
|---|---|---|---|
| 227 | 2,4-(CH₃)₂-5-SO₃H-phenyl-CO-(4-Cl-3-CH₃-phenyl) | | bluish red |

TABLE 14-continued

[Structure: naphthalene with $H_2N$, $Q^2-N=N-$, $HO$, and $SO_3H$ substituents]

| Example No. | Q² | λ$_{max}$ [nm] (in water) | Hue |
|---|---|---|---|
| 228 | [2,5-diisopropyl-4-sulfophenyl-CO-O-(3-methylphenyl)] | | bluish red |
| 229 | $C_7H_{15}(n)$-phenyl-CO-O-(3-methyl-4-sulfophenyl) | 513 | bluish red |
| 230 | cyclohexyl-H-phenyl-CO-O-(3-methyl-4-sulfophenyl) | 513 | bluish red |
| 231 | $C_9H_{19}(n)$-phenyl-CO-O-(3-methyl-4-sulfophenyl) | 513 | bluish red |
| 232 | $C_{11}H_{23}(n)$-phenyl-CO-O-(3-methyl-4-sulfophenyl) | 513 | bluish red |
| 233 | $C_9H_{19}(n)$-CH(CH$_3$)-phenyl-CO-O-(3-methyl-4-sulfophenyl) | 513 | bluish red |
| 234 | $C_8H_{17}$-(2-methylphenyl)-CO-O-(3-methyl-4-sulfophenyl) | 513 | bluish red |

TABLE 15

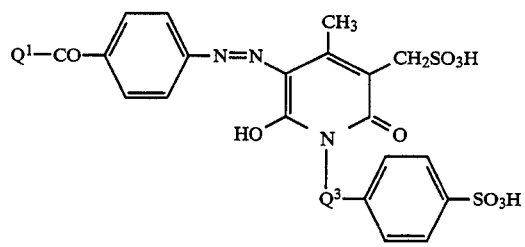

| Example No. | $Q^1$ | $Q^3$ | Hue |
|---|---|---|---|
| 235 | ![3,4-dimethylphenyl] | $CH_2$ | greenish yellow |
| 236 | ![3,4-dimethylphenyl] | $C_2H_4$ | greenish yellow |
| 237 | ![2,5-dimethylphenyl] | $CH_2$ | greenish yellow |
| 238 | ![2,5-dimethylphenyl] | $C_2H_4$ | greenish yellow |

EXAMPLE 239

257 g of 1-(2-phenylethyl)-6-hydroxy-3-cyano-4-methylpyrid-2-one were added at not more than 70° C. to a mixture of 160 g of 100% by weight sulfuric acid and 380 g of 24% by weight oleum. The solution formed was subsequently stirred at 75° C. for 5 hours, producing essentially a product of the formula

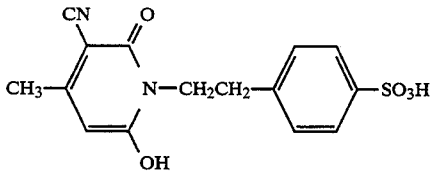

This was followed by heating at 110° C. for 5 hours, during which the cyano group hydrolyzed and the carboxylic acid intermediate was decarboxylated (foaming due to $CO_2$ evolution ). Then the reaction mixture was heated to 130°–135° C. and stirred at that temperature for 5.5 hours. After the reaction mixture had cooled down to about 110° C., it was stirred out onto about 900 g of ice-water, and the compound of the formula

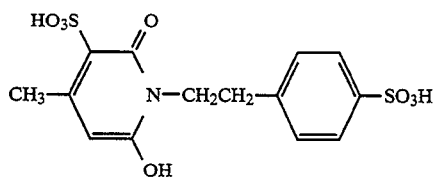

was neutralized at ≦30° C. with sodium hydroxide solution. This solution can be used directly for preparing azo dyes. $\lambda_{max}$ ($H_2O$): 325 run, 247 run, (minimum at 280 and 235 nm).

We claim:

1. A pyridone compound of the formula II

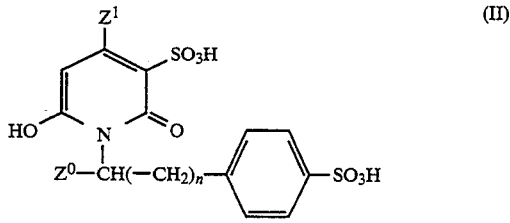
(II)

where n is 1 or 2, $Z^0$ is hydrogen or $C_1$-$C_4$-alkyl, and $Z^1$ is hydrogen, $C_1$-$C_4$-alkyl or phenyl.

2. A process for preparing a pyridone compound of the formula IIa

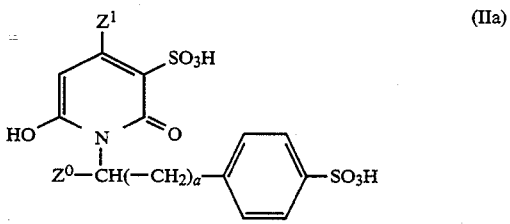
(IIa)

where a is 0, 1 or 2, $Z^0$ is hydrogen or $C_1$-$C_4$-alkyl, and $Z^1$ is hydrogen, $C_1$-$C_4$-alkyl or phenyl, by reacting a pyridone of the formula IIb

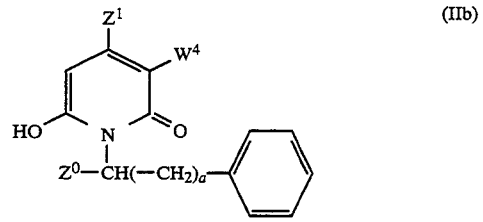
(IIb)

where $W^4$ is cyano or acetyl and a, $Z^0$ and $Z^1$ are each as defined above, with oleum, wherein said oleum contains from 1 to 2 mol of free sulfur trioxide and said reaction comprising a first stage at from 0° to 75° C. for from 1 to 5 hours and then a second stage at from 80° to 135° C. for from 2 to 11 hours.

* * * * *

UNITED STATES PATENT AND TRADEMARK OFFICE
CERTIFICATE OF CORRECTION

PATENT NO. : 5,380,859
DATED : January 10, 1995
INVENTOR(S) : Gunther Lamm et al.

It is certified that error appears in the above-indentified patent and that said Letters Patent is hereby corrected as shown below:

On the title page, Item [75],

The second inventor's last name is spelled incorrectly, should read: --Reichelt--

Signed and Sealed this

Eighteenth Day of April, 1995

*Attest:*

BRUCE LEHMAN

*Attesting Officer*

*Commissioner of Patents and Trademarks*